United States Patent [19]
Saltzstein et al.

[11] Patent Number: 5,941,829
[45] Date of Patent: Aug. 24, 1999

[54] CONCURRENT MEDICAL PATIENT DATA AND VOICE COMMUNICATION METHOD AND APPARATUS

[75] Inventors: William E. Saltzstein, Amity; Damon J. Coffman, Portland; Scott M. Burkhart, Hillsboro, all of Oreg.

[73] Assignee: Instromedix, Inc., Hillsboro, Oreg.

[21] Appl. No.: 08/957,669

[22] Filed: Oct. 24, 1997

Related U.S. Application Data

[63] Continuation of application No. 08/556,468, Nov. 8, 1995, Pat. No. 5,704,364.

[51] Int. Cl.$^6$ .............................. A61B 5/04; A61B 5/0402
[52] U.S. Cl. .......................... 600/509; 600/508; 128/904
[58] Field of Search ................................... 600/508, 509; 128/904

[56] References Cited

U.S. PATENT DOCUMENTS

| | | |
|---|---|---|
| 3,886,314 | 5/1975 | Pori . |
| 4,126,462 | 11/1978 | McGrath et al. . |
| 4,173,971 | 11/1979 | Karz ........................................ 600/515 |
| 4,494,553 | 1/1985 | Sciarra et al. . |
| 4,531,527 | 7/1985 | Reinhold, Jr. et al. ................. 600/509 |
| 4,784,162 | 11/1988 | Ricks et al. . |
| 4,803,625 | 2/1989 | Fu et al. . |
| 4,838,275 | 6/1989 | Lee . |
| 4,933,873 | 6/1990 | Kaufman et al. . |
| 4,945,477 | 7/1990 | Edwards . |
| 4,967,756 | 11/1990 | Hewitt . |
| 5,007,429 | 4/1991 | Treatch et al. . |
| 5,012,814 | 5/1991 | Mills et al. . |

(List continued on next page.)

FOREIGN PATENT DOCUMENTS

| | | |
|---|---|---|
| 122888 | 10/1984 | European Pat. Off. ............... 600/508 |
| 0645710A2 | 7/1994 | European Pat. Off. . |
| 0 656 718 | 7/1995 | European Pat. Off. . |
| 0645710A3 | 11/1995 | European Pat. Off. . |

OTHER PUBLICATIONS

James E. McKee, Noel E. Evan and Frank J. Owens, A simultaneous Full–Duplex Speech and Electrocardiogram Communications System, Proceedings of the Annual International Conference of the IEEE Engineering in Medicine and Biology Society, Baltimore, Nov. 3–6, 1994, vol. 16, pp. 902–903.

(List continued on next page.)

Primary Examiner—William E. Kamm
Assistant Examiner—Carl H. Layno
Attorney, Agent, or Firm—Klarquist Sparkman Campbell Leigh and Whinston, LLP

[57] ABSTRACT

Method and apparatus for voice interaction between the service provider to the patient whose life signs, e.g. an electrocardiograph (ECG), concurrently are being monitored are described. Patient data, and preferably patient waveform data, and voice communication are conveyed in real-time on a single, or common, public switched telephone (PSTN) line. A life signs monitor at the patient site is connected to the patient and to a digital simultaneous voice and data (DSVD) device having the ability to digitize and compress the patient's voice and having the ability to decompress and analogize the physician's voice via a standard telephone. A modem modulates and demodulates transmitted and received data over the telephone line. At a remote monitoring site a second modem receives and transmits data over the same telephone line. The second modem is connected with a second DSVD device connected to a display- or printer-equipped receiving station for presentation in textual or graphic form to a remote service provider the patient data, e.g. in the form of an ECG trace. Thus, the service provider has the ability to overview patient life signs monitoring while in real-time, synchronized vocal communication with the patient, and therefore is able to correlate the patient's mental, physical and emotion state with the data being received, as well as for instructing the patient or otherwise reassuring the patient of the proper use of the life signs monitor or diagnosing or prescribing in real-time a response to what is gleaned from the monitoring.

25 Claims, 4 Drawing Sheets

U.S. PATENT DOCUMENTS

| | | |
|---|---|---|
| 5,024,225 | 6/1991 | Fang . |
| 5,033,474 | 7/1991 | Varelis et al. . |
| 5,038,800 | 8/1991 | Oba . |
| 5,063,513 | 11/1991 | Greenblatt . |
| 5,128,552 | 7/1992 | Fang et al. . |
| 5,142,484 | 8/1992 | Kaufman et al. . |
| 5,216,596 | 6/1993 | Weinstein . |
| 5,321,618 | 6/1994 | Gessman . |
| 5,339,823 | 8/1994 | Reinhold, Jr. ............ 600/509 |
| 5,343,869 | 9/1994 | Pross et al. . |
| 5,357,427 | 10/1994 | Langen et al. . |
| 5,381,798 | 1/1995 | Burrows . |
| 5,390,238 | 2/1995 | Kirk et al. . |
| 5,394,882 | 3/1995 | Mawhinney . |
| 5,462,051 | 10/1995 | Oka et al. . |
| 5,467,773 | 11/1995 | Borgelson et al. . |
| 5,474,090 | 12/1995 | Begun et al. ............ 600/520 |
| 5,544,661 | 8/1996 | Davis et al. . |
| 5,553,609 | 9/1996 | Chen et al. . |
| 5,557,800 | 9/1996 | Kasimov et al. . |
| 5,613,495 | 3/1997 | Mills et al. . |
| 5,785,650 | 7/1998 | Akasaka et al. . |
| 5,842,978 | 12/1998 | Levy . |

OTHER PUBLICATIONS

William Stallings, Data and Computer Communications, 2d. Ed., pp. 103–113, MacMillan Publishing Co., 1988.

Bernard L. Segal et al., Telephone Phonocardiograph, *The American Journal of Medical Electronics*, pp. 189–191, Jul.–Sep. 1964.

Fisher, Anne B., House Calls, Inc., pp. 72–79, Jul. 1989.

Comparison of Duplex and Triplex Memory Reliability, pp. 503–507, IEEE Transactions on Computers, vol. 45, No. 4, Apr. 1996.

Symposium on the Engineering of Computer–Based Medical Systems, pp. 22–27, Jun. 8–10, 1998.

English language abstract of published European Patent Application No. 645,710A2, Derwent Info. Ltd.

CONCURRENT MEDICAL PATIENT DATA AND VOICE COMMUNICATION METHOD AND APPARATUS

RELATED APPLICATION

This is a continuation of our similarly titled, application, Ser. No. 08/556,468, which was filed on Nov. 8, 1995 and issued as U.S. Pat. No. 5,704,364 on Jan. 6, 1998. The disclosure of Ser. No. 08/556,468 is hereby incorporated by reference.

BACKGROUND AND SUMMARY OF THE INVENTION

The invention generally relates to remote medical patient monitoring. More particularly, it involves real-time communication of patient data, and especially waveform data, over a single telephone line concurrently with both medical practitioner and patient voice.

Increasingly, medical patients are provided with portable, patient-proximate monitoring and control equipment that, in turn, is connected to a remote (typically centralized) healthcare provider, e.g. a physician, skilled technician or other service provider. Typically, patient vital sign data, e.g. an electrocardiograph (ECG) waveform, is digitized and transmitted over a phone line to the remote monitoring site for diagnostic, oversight and recording purposes. Conventionally, digital transmission protocols for use on voice-grade communications channels such as the public switched telephone network (PSTN) or cellular telephone network (CTN) use the entire available bandwidth for data transmission. This precludes the use of the phone for voice interaction between the physician and the patient.

To make the patient feel at ease, it is important to both the patient and the physician to interact the way they would during an office visit. Such interaction provides the physician with an opportunity to follow up any observations with questions to help diagnose the condition of the patient, as well as to offer reassurances and any needed instruction regarding in the patient's use of the monitoring equipment. Similarly, it is important that the voice and patient data are transmitted in real-time so the medical practitioner is able to correlate the patient's activities and comments with the transmitted patient data. For example, a patient may be in a variety of psychological and physiological states that affect the data being collected, which otherwise may appear abnormal or otherwise significant when it is analyzed by a practitioner who does not know this event occurred while the data was being collected. Similarly, equipment problems also may lead to data which appears to reflect significant or life-threatening patient conditions, but can be identified and remedied almost immediately if the practitioner is in real-time communication with the patient.

To further explain the need for real-time measurement and communication of patient data concurrently with physician and patient voice, it is necessary to differentiate real-time voice communication with underlying, delayed data communication from systems that concurrently transmit real-time voice and real-time data. As discussed in more detail below, a system that uses a single telephone line for real-time voice communication between physician and patient while previously measured and stored data is transmitted, or interleaved, in the available bandwidth is dramatically different from a system that enables concurrent real-time voice and real-time data communication over a single communication line. The first enables the physician and patient to interact and respond to each other, as well as the physician to receive patient data while this interaction is occurring. The limitation of this system, however, is that the patient is receiving and viewing patient data which is not synchronized with the interaction between the physician and the patient. Instead, data is measured, stored and transmitted in available bandwidth, which can result in a defined duration of data taking much longer than that time duration to be transmitted and received. Unless the patient voice and data are synchronized, the physician is unable to correlate the received patient data with the patient's current bodily activities, mental state and physical condition.

Similarly, it is necessary to discuss the concept of "real-time" communication of voice and data. As discussed subsequently, this term appears to be used fairly loosely in other references to describe communication that occurs over a common communication link, without concerns or import given to the time lapse between the time data is collected from a patient and the time the data is received by a diagnostician, or to pauses or other system-required delays between communications. As used herein with respect to the present invention, it should be understood that real-time communication is meant to refer to virtually instantaneous transmission, which preferably means less than one second between the capture and transmission of the data and voice. Less preferably, but still within the scope of this term are communications which take up to a few seconds. Anything beyond this, such as 10 seconds, a minute, sixty minutes, etc. is not considered to be real-time communication, as used herein.

The requirements for a system to transmit concurrently this synchronized, real-time voice and data are further identified and distinguished when the patient data is waveform data. By way of background, U.S. Pat. No. 5,012,814 to Mills et al. for an implantable-defibrillator pulse detection-triggered ECG monitoring method and apparatus describes the characteristics, including duration and principal components, of a typical ECG waveform. The disclosure of Mills et al. is hereby incorporated by reference. In Mills et al., a typical ECG waveform, which includes a recurrent portion (centrally shown in the illustrated trace) commonly referred to as a QRS complex, and implantable cardioverter/defibrillator (pacemaker) pulse are shown, respectively, in FIGS. 3A and 3B. In column 5, lines 28–49, the typical duration of the waveform and pulse are discussed. Specifically, the QRS complex may last for up to 100 milliseconds, while a typical pacemaker pulse lasts only a few milliseconds.

Therefore, to record and transmit either of these waveforms in a continuous, graphical representation, a patient monitoring system must be capable of measuring, recording and transmitting data taken in sufficiently small increments, or preferably continuously, to permit the waveform, including any and all peaks, troughs or aberrations therein, to be accurately reconstructed or traced. The method and apparatus disclosed herein satisfies this requirement, as discussed subsequently, with its capability for graphical waveform data and at least one-way voice communication to be simultaneously transmitted in real-time over a single telephone line. The data is measured at a sufficiently high frequency (time resolution) and accuracy (amplitude resolution) to allow the patient's vital sign waveform to be reproduced, or "traced," after transmission for diagnosis and analysis by the practitioner. Such frequency and accuracy requirements are in compliance with applicable known standards such as ANSI/AAMI EC-11, EC-13, EC-38 and SP10; IEC1099; etc., familiarity with which is assumed.

Therefore, to transmit real-time, or synchronized, patient data and single or duplex voice communication over a single communication line, a system not only must be able to measure monitoring and/or diagnostic quality waveform data so that it can be reproduced after transmission, but also must be able to synchronize this data with single or duplex voice communication over the limited bandwidth of a single communication line. Several recent patents have attempted to address these problems, yet as discussed, fail to allow concurrent, real-time transmission of voice and monitoring or diagnostic quality waveform data over a single communication line.

For example, U.S. Pat. No. 5,553,609 to Chen et al. is entitled "Intelligent Remote Visual Monitoring System for Home Health Care Service." Chen et al. disclose a system for home health care monitoring which includes a Slave Monitoring Station 26 utilizing a personal computer and modem 76 for digitizing and communicating voice and patient information to a remote Master Monitoring Station 24 over a single telephone line, as shown in FIG. 7. The patient data consists of video images taken by camera 68, and the patient audio is detected by microphone 72. The video images and the audio are compressed digitally at one station and then decompressed at the other to reduce the bandwidth during communication.

The system of Chen et al., however, is only capable of sampling or measuring at rates of up to 15 frames per second. This rate may be suitable for freeze-frame video images, however grainy and jerky, but it will not suffice to communicate patient waveform data to a medical practitioner. For example, if a typical ECG waveform, with a QRS complex lasting less than 100 milliseconds, was measured at a rate of 15 samples per second, no more than two samples could be taken over the entire QRS complex. Furthermore, if this data were presented in a graphical, time-dependent format, the intermittent, spaced-apart readings would likely omit vital information necessary to diagnose specific medical conditions, such as tachycardia and ischemia. In addition, a practitioner would often be unable to determine which waveform a particular sample came from because of the missing transition regions between readings. Perhaps this is why Chen et al. disclose replacing the video equipment with medical sensors that only detect static or averaged values, such as weight, body temperature and pulse rate, which are relatively stable and may be adequately measured and communicated using the sampling rate provided by the system of Chen et al. These static or relatively static measurements are not waveform data, much less diagnostic waveform data. Because only video clips or averaged, static data values are measured and transmitted by the system of Chen et al., this perhaps also explains why Chen et al. do not disclose any form of meaningful error detection with respect to the measured data.

Similarly, U.S. Pat. No. 5,544,661 to Davis et al. is entitled "Real Time Ambulatory Patient Monitor" and discloses a cellular system for monitoring patient waveform data, comparing the data to stored threshold values and contacting a central monitoring station if the measured data exceeds the threshold values. If so, the system establishes communication with the central station and transmits the previously measured data to the station while allowing two-way communication between the station and the patient. Despite its title, however, the patent to Davis et al. only discloses and enables real-time voice communication, with the stored buffer of patient data being interleaved to fit within any remaining bandwidth for transmission to the central station.

The system disclosed by Davis et al. measures patient data, including 3-lead ECG and plethysmograph, compares the data to stored threshold values and stores the data in a sixty minute buffer. If the data exceeds the threshold value, the system activates a cellular unit and establishes communication with the central station. Once this communication is established, two-way voice communication between the patient and the station is possible, while the previously stored data is multiplexed and interleaved with the voice communication. As shown in FIG. 9, the patient's data is measured, then compressed and stored in a one hour buffer, where it can be accessed if needed. FIG. 11 demonstrates how the stored, prerecorded data is multiplexed and interleaved with the two-way voice communication to let the practitioner see the data that was collected before communication was established between the practitioner and the patient. While the data may not be days or even hours old, it is not "real-time" data, which requires measurement and transmission within seconds of each other. The data is minutes or even an hour or more old when transmitted to the central station. Therefore, there is no correlation with the patient's current physical state or condition, and it will not be possible to explain data which may have resulted simply from a patient experiencing an excited or elevated psychological or physiological state, or from the life signs equipment malfunctioning or becoming disconnected from the patient. Furthermore, when the data is not transmitted in real time or synchronized with the voice communication, such communication is much easier and less demanding on the already limited bandwidth of a single communication line. This is largely because the data can be stretched or spread out to transmit over a longer period of time to reduce the bandwidth necessary at any given moment to transmit the data.

Furthermore, the system of Davis et al. provides no detection for erroneously measured data. As discussed, if the measured data exceeds previously set baseline values, the system automatically establishes communication with a central station to open a two-way voice channel between the patient and the central station and to transmit the data. The measured data is stored within various buffers until transmitted to the central station or discarded. Each of the buffers is used to store different measurements, which are subsequently and separately compared to respective stored threshold values to determine if a life-threatening condition exists. As shown schematically in FIGS. 13 and 14 and explained in col. 7, line 50 to col. 8, line 38, of Davis et al., the buffers each store a different type of information. Specifically, as indicated at 1407 in FIG. 14, each buffer stores data relating to one of the following groups: S-T deviation, QRS width and rate, T wave amplitude and polarity, plethysmograph rate and amplitude. Each of these different measurements or values are then compared to separate, stored threshold values at 1408 in FIG. 14. If the measured value is greater than the threshold value, then the monitoring station is notified using a cellular connection. Besides the fact that the buffers disclosed in Davis et al. provide no protection against erroneous data, the entire system disclosed in Davis et al. neither describes nor suggests any mechanism for detecting erroneously measured or recorded data. Therefore, if the data stored in any one of the previously discussed buffers is erroneous, it could cause the system to alert the monitoring station, which in turn will erroneously alert the patient that the patient may be in a life-threatening situation. This false alarm to the patient may in fact trigger an actual medical emergency in the patient. This alone demonstrates why the invented error detection technique disclosed herein represents a significant improvement over conventional patient monitoring systems.

Thus, it is a principal object of the present invention to provide at least for concurrent digital medical patient data and voice communication over a single, duplex communication line.

It is another object of the invention to provide such digital and voice communication over the public switched telephone network (PSTN).

Yet another object is for such communication to include the communication of patient waveform data.

Still another object is to provide such communication within real-time limits of when the patient data is obtained.

Another important object of the invention is to provide such communication with high data and voice integrity.

Yet another object is to render the communication link's bandwidth automatically dynamically allocable to variable demand as between data and voice.

It is another object of the invention to provide also for the communication over such a line of digital video information in real time at a useful refresh rate.

Another object is to provide combined voice channels over the same single physical channel on which medical patient data is carried.

Still another object of the invention is to provide for the communication of medical patient data that is synchronized with the patient's voice communication to the practitioner.

Briefly, the invented apparatus enables patient waveform and other data to be measured and concurrently transmitted in real-time with at least one-way voice communication between the medical practitioner and the patient over a single, usually common, communication line. In preferred embodiments of the apparatus, two-way concurrent voice and data communication is established. Patient life signs equipment at the patient site is connected to the patient and to a DSVD device having the ability to digitize and compress the patient's voice and having the ability to decompress and render in analog form the physician's voice via a standard telephone. A modem modulates and demodulates transmitted and received data over the telephone line. At a remote monitoring site a second modem receives and transmits data over the same telephone line. The second modem is connected with a second DSVD device connected to a display- or printer-equipped receiving station for presentation of the patient waveform or other data, e.g. in the form of an ECG trace, in textual or graphic form to a remote service provider. Thus, the service provider has the ability to overview patient life signs data obtained while in direct vocal communication with the patient. The data and voice are synchronized and transmitted in real time, enabling the physician to account and correct for the patient's current physical or emotional state, as well as for instructing the patient or otherwise reassuring the patient of the proper use of the life signs monitor or diagnosing or prescribing in real time a response to what is learned from the monitored data.

These and other objects and advantages of the invention will be more clearly understood from a consideration of the accompanying drawings and the following description of the preferred embodiment.

DETAILED DESCRIPTION OF THE PREFERRED EMBODIMENTS AND METHODS OF USING THE SAME

Figure 1:
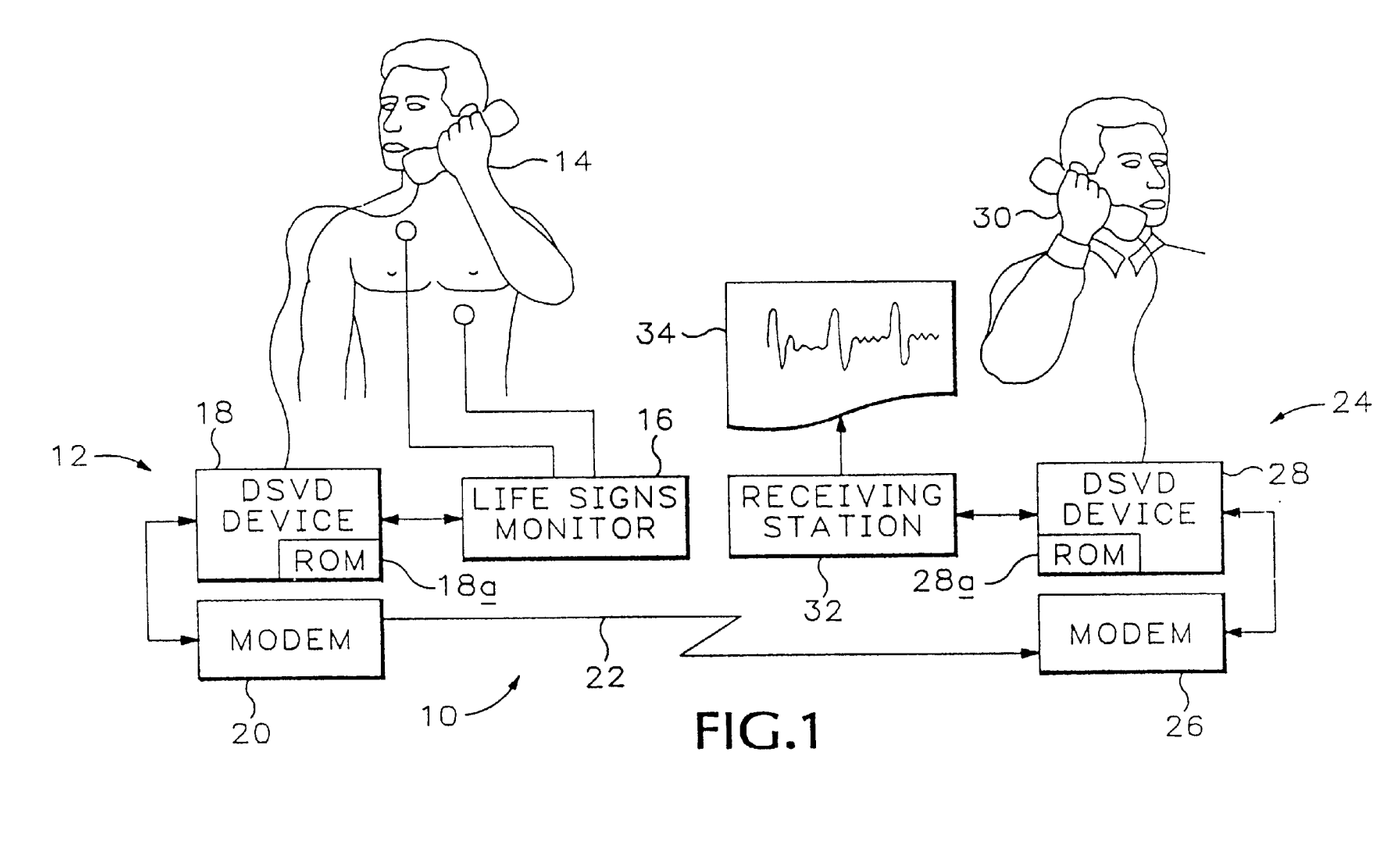
FIG. 1 is a system block diagram of the invented apparatus made in accordance with a preferred embodiment.

Referring first to FIG. 1, the invented apparatus made in accordance with its preferred embodiment is indicated generally at 10. At a patient site indicated generally at 12, a patient 14 is operatively connected to patient life signs equipment, such as a life signs monitor 16. As shown in FIG. 1, the patient life signs equipment includes an electrode-equipped ECG monitor that senses the patient's skin potential variations, digitizes the signal and optionally records the digitized ECG waveform in an integral memory for immediate or deferred playback. It will be appreciated that life signs monitor 16 may be equipped to monitor any one or more desirable life signs, including vital signs such as 12-electrode ECG, EEG, pulse rate, blood pressure (bp), blood oxygen level (pulse oximetry), blood sugar level (glucometry), lung capacity (spirometry), etc., although only 2-electrode ECG monitoring is illustrated in FIG. 1. Life signs monitor 16 is operatively connected with a digital simultaneous voice and data (DSVD) device 18 that is capable of digitizing, compressing and time interleaving voice and data for transmission via a modem 20 over a single telephone line 22.

Preferably, DSVD device 18 supports duplex concurrent voice and data, thereby supporting at least a one-way instructional voice monologue from a remote physician, skilled technician or other service provider, and most preferably supporting a voice dialogue between patient 14 and the remote service provider. Importantly, such is rendered possible over a single, common telephone line, thereby obviating the need for more than one and making remote monitoring practical to at-home vital sign monitor patients. Such is the province of DSVD devices such as those available from AT&T (VoiceSpan™), Intel (ProShare™), U.S. Robotics, Inc. (Sportster Vi™) and Multi-Tech Systems, Inc. (MultiModem PCS®), all of which support concurrent digitized voice and data communication over the public switched telephone network (PSTN). Those skilled in the art will appreciate that any suitable DSVD device, whether it is so-called or whether it merely performs such functions as are described herein, is contemplated for use in invented apparatus 10, and is within the spirit and scope of the invention.

Preferably, in accordance with the invention, DSVD device 18 is specially equipped with error correction software or firmware 18a, preferably residing in its read and write memory (RAM) or read-only memory (ROM), that ensures the integrity of the patient data obtained from life signs monitor 16 or modem 20. Those of skill in the art will appreciate that such memory preferably may be any relatively high-density, low-cost volatile or non-volatile memory such as a block re-programmable, so-called "FLASH" memory device. Typically, modem 20 would provide some level of error correction, but it is important with patient data that the lowest possible bit error rate (BER) and frame error rate (FER) is maintained. Skilled persons will appreciate that the use of DSVD device 18 is only one currently preferred embodiment and that alternative embodiments nevertheless are within the spirit and scope of the invention. It will also be appreciated that the functions performed, in accordance with the preferred embodiment of the invention, in firmware residing within DSVD 18 alternatively may be performed by a central processor that is programmed to provide for the control of life signs monitor 16 and modem 20, as well as to perform the needed DSVD tasks, and that all such functions may be performed, within the spirit and scope of the invention, in software, firmware, hardware or any combination thereof.

One important aspect of the invention involves a patient data communication protocol that provides for automatic data validation by way of detection of transmission or reception errors. Preferably, the validation or verification technique includes serially communicating the patient data two or more times in succession, with identical patient data being accompanied by orthogonal error detection codes embedded within packet headers. An error that propagates through one error detection processor (however unlikely such may be) is rendered orders of magnitude less likely by the fact that the second error detection code is independent of the error methodology that permitted the error to propagate through the first processor. This invented technique is described herein as serial double fault tolerance. As will be seen, in accordance with the invention, if and only if data are error-free will they be transmitted and if and only if data are error-free upon their reception will they be permitted to affect patient diagnosis and treatment. Otherwise, the data will be flagged as being anomalous and no action will be indicated unless and until further valid medical patient data are transmitted and received without error. Such may be thought of as a zero-fault tolerance scheme.

Standards have been established for critical monitoring data communications. One such example is TÜV which stands for Technischer Überwachungsverein (which roughly translates into Technical Over-seeing Body), a German model for such communications applications that has been adopted by the European Community, familiarity with which is assumed. Generally, the TÜV standard requires that data representative of critical monitoring information such as patient vital signs be locally stored for transmission in at least two memory locations for local comparison and verification purposes. Those of skill in the art will appreciate, however, that the would-be identical data in the various locations in memory may be corrupted and yet may be in agreement with one another such that one or more data errors exists but is undetected.

Alternatively or additionally to the preferred patient data error correction technique described above, patient data integrity may be assured by a service provider, who may perform patient data oversight while in voice communication with the patient. For example, a physician or skilled technician or other service provider who notes an apparently anomalous ECG waveform, very simply and without additional cost in accordance with the present invention, may instruct or request that the patient or patient device re-transmit the dubious data that has been recorded by the patient equipment. The human factor thus provides a significant advantage over conventional life signs monitoring that relies solely on communication electronics and/or protocols to ensure data integrity. It is unlikely that a temporary adverse condition of a telephone line, e.g. a momentary carrier disruption, would occur twice in short succession. Thus, a subsequent transmission of patient data that was corrupted by such a condition of the communication conveyance typically would result in a successful transmission of accurate patient data, yet in real-time (albeit slightly delayed) response to what might be a life-threatening condition for the monitored patient.

Referring still to FIG. 1, it may be seen that telephone line 22 is connected at a remote monitoring site, indicated generally at 24, to a second modem 26 which may be identical to modem 20. A second DSVD device 28 operatively connected to modem 26 performs essentially the same functions as DSVD device 18 at patient site 12. Second DSVD device 28 also preferably is equipped with specialized error correction firmware residing in a ROM 28a integral with second DSVD device 28. DSVD device 28 includes a voice port for at least one-way, and preferably two-way, voice communication by a physician, skilled technician or other service provider 30. Operatively connected with DSVD device 28 is a receiving station 32 capable of producing a display or printout 34 of tabulated data, ECG traces or other textual or graphic illustrations of the monitored life signs of patient 14, e.g. the ECG waveform shown in FIG. 1. Thus, in accordance with the invention, service provider 30 is able not only to overview a patient's monitored life signs, but also to vocally interact with the patient during such overview.

Those of skill in the art will appreciate that DSVD device 18 and modem 20 may be integral with one another, and may be packaged as a stand alone unit or as a board that may be installed in a personal computer (PC) or workstation. Similarly, DSVD device 28 and modem 26 may be integral with one another, and may be similarly packaged. As mentioned above, it is contemplated also that the functions of DSVD 18 may be performed instead by an application program executing on a PC having no DSVD per se but having the required signal processing capabilities. It will also be appreciated that life signs monitor 16 may be integral with DSVD device 18 or may be a board that may be installed in such a PC or workstation located at patient site 12. Similarly, it will be appreciated that receiving station 32 may be equipped with an integral display or printer for producing display or printout 34, and that receiving station 32 may be integral with DSVD device 18 or may be a board that may be installed in such a PC or workstation located at monitoring site 24. Life signs monitor 16 alternatively may be worn by patient 14 as a neck-worn pendant or wrist-worn watch, and it may wirelessly communicate patient data to DSVD device 18. Those skilled in the art will appreciate that DSVD devices 18, 28 may have integral microphones and speakers to provide patient 14 and service provider 30, respectively, with a hands-free voice communication alternative to a standard telephone handset. Of course, as discussed herein, such a handset may be replaced or augmented with a stethoscope forming a part of a telephone or having a built-in microphone or other transducer capable of converting audio vibrations to an electrical signal. All such alternative configurations and their functional equivalents are within the spirit and scope of the invention.

Those of skill in the art now may appreciate that the invented method and apparatus promote better voice communication between physician and patient. Most homes have only one telephone line, and previously there has been no possibility of concurrent voice communication between a physician and a patient who is being transtelephonically monitored. With the present invention, voice communication is possible during a monitoring session. For example, a physician might inquire of the patient during vital signs monitoring of the patient's general health, whether the patient has been taking prescribed medications, regarding the patient's diet and regularity, e.g. urinary or bowel movement, etc. Such information is vital to an assessment of the patient's well-being, and may greatly assist the physician in interpreting the monitored vital signs. It also tends to place the patient at greater ease during what for some is a stressful monitoring session. Thus, more full service remote diagnosis and treatment of patients is possible by use of the invented method and apparatus. Perhaps more importantly, the practitioner is able to correlate and better understand the received patient data because the practitioner can detect independently, or if necessary ask questions about the patient's emotional, physical and mental state while the data is being obtained. Therefore, sudden exertions, exciting moments or bodily functions will be apparent to the practitioner and can be accounted for, or discounted, when interpreting the received data.

Figure 2:
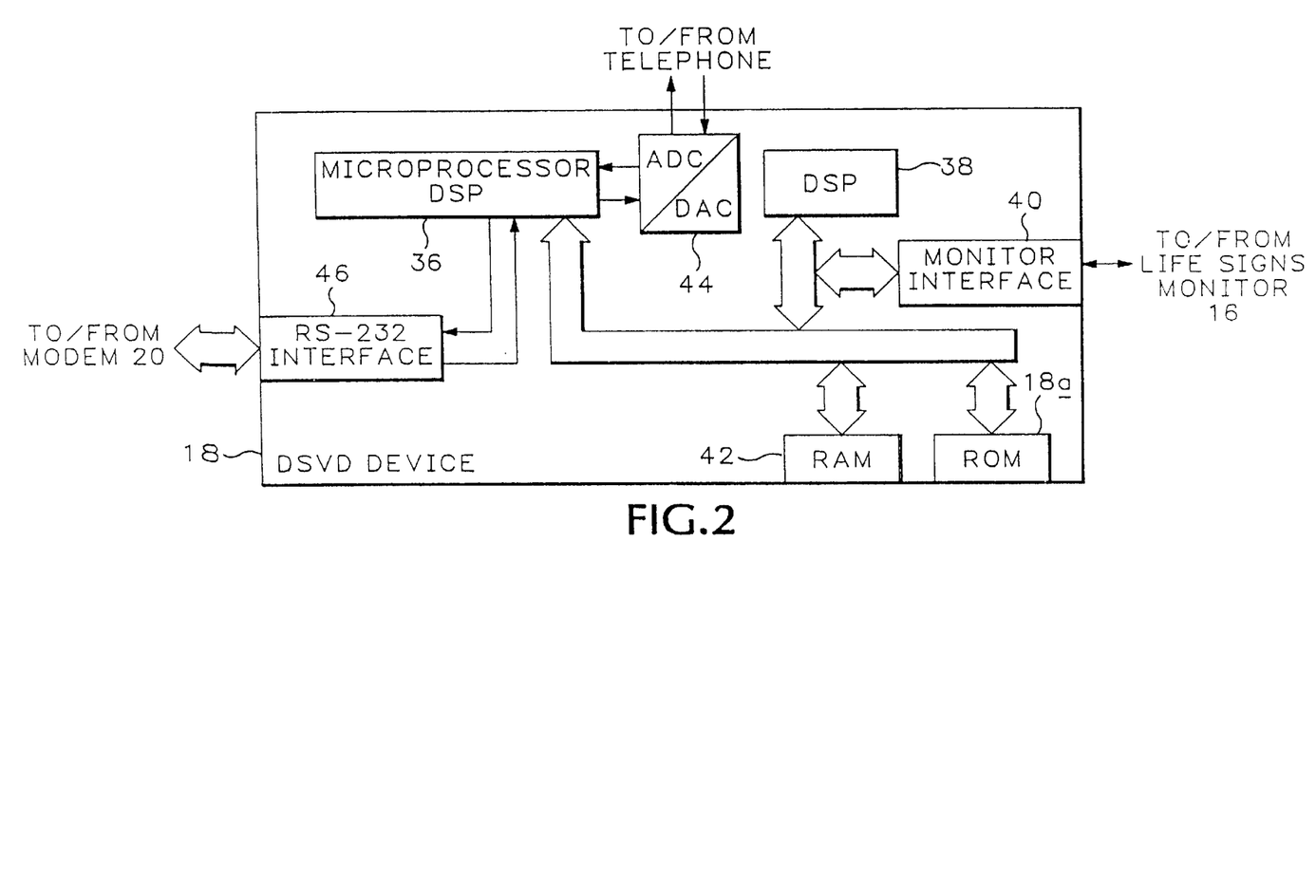
FIG. 2 is a detailed schematic diagram of one of the digital simultaneous voice and data (DSVD) devices shown in FIG. 1.

Turning now to FIG. 2, DSVD device 18 will be described by reference to a detailed schematic diagram. (Those skilled in the art will appreciate that DSVD device 28 would be substantially identically described and illustrated, with RS-232 and digital interface connections instead to modem 26 and to receiving station 32.) In addition to ROM 18a, DSVD device 18 preferably includes a microprocessor (μPROCESSOR) 36, a digital signal processor (DSP) 38, a life signs monitor interface 40 connectable, in turn, to life signs monitor 16 (not shown in FIG. 2, but shown in FIG. 1) and a read-and-write memory (RAM) 42 all connected to a common data/address bus as indicated by the broad lines. Microprocessor 36 also has an input/output (I/O) port connected to an analog-to-digital converter (ADC) and digital-to-analog converter (DAC) 44 connectable, in turn, to a telephone (not shown in FIG. 2, but shown in FIG. 1). Finally, microprocessor 36 has an I/O port connected to an RS-232 or similar, preferably EIA-standard, interface 46 connectable, in turn, to modem 20 (not shown in FIG. 2, but shown in FIG. 1).

Figure 3:
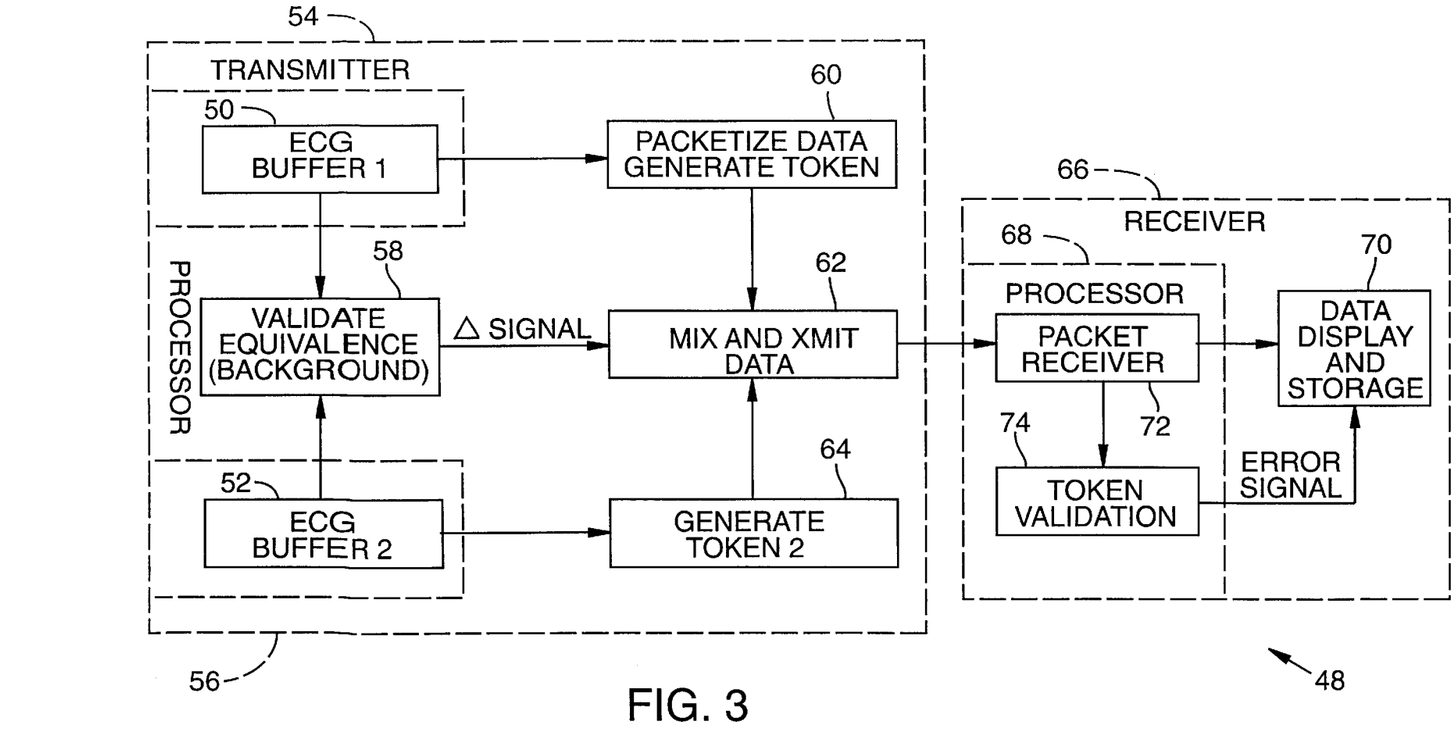
FIG. 3 is a schematic block and data flow diagram illustrating the invented medical data verification method and apparatus of the invention.

Referring now to FIG. 3, invented apparatus for telecommunicated medical data verification is indicated at 48. In accordance with this feature of the invention, medical data error rates are reduced to near-zero by the use of what will be referred to herein as serial double fault error-prevention technique. By way of background, it will be appreciated that current serial data communication has achieved a level of integrity whereby corrupted data reception already is highly improbable. Typically utilized techniques involve cyclic redundancy checking (CRC) of transmitted data by appending to the transmitted data packet a unique code that is a boolean combination of the data that is transmitted, whereby a receiver performs a checksumming by similar combination to detect corrupted data bits within the received data stream. If uncorrectable data errors are detected by the receiver, typically the communication protocol requires retransmission of the data packet until an uncorrupted, or at least a correctable, data packet is received. Of course, such retransmissions, or retries, result in degraded data throughput, which depending upon the level of degradation can seriously impact applications which are dependent upon the timely arrival of uncorrupted data at the receiver.

Communication channels that introduce chaotic noise to the communication of life critical data have not been adequately addressed by conventional data error detection/correction techniques and protocols. The invented serial double fault technique may be used in applications where hardware, software or firmware (or a combination thereof) acquires critical data, and renders potentially life-sustaining and life-threatening decisions based thereon. The invented technique borrows somewhat from mathematical or logical redundancy theory, and is akin to getting a second medical opinion before proceeding with an extensive or intensive therapeutic or surgical procedure. In a preferred embodiment of the invention, dual processors monitor critical life data and produce—by independent techniques—a key or token derived therefrom and then compare their results prior to any data-based decision making. Only if the two independent processors agree that critical life data is uncorrupted is a life-critical action initiated by the processors on the basis of the data. Importantly, the independence of the processors that derive the key or token is ensured by the way in which they are designed, preferably by independent design teams in a "clean room" environment. Absent agreement between the two independent processors, i.e. without unanimity of 'opinion' regarding a patient prescription, professional intervention is invoked as by annunciating to a competent medical practitioner the inability of the processors to agree on a prescribed course of action.

In accordance with a preferred embodiment of the invention, a key or token is embedded in each logical data packet that is communicated. A separate data packet containing a complementary key is transmitted synchronously or asynchronously relative to each of the first packets. The receiving station validates the complementary of the two keys via execution of an independent algorithm. This provides a first level of reliability in life critical data communication, all but eliminating random line noise data corruption.

A second level of reliability is ensured by the way in which keys or tokens are created. Each of two keys—a primary and a complementary key—is created by a different technique or algorithm from data residing at the transmitter in different data stores or memory buffers. By generating the keys by diverse methods from diverse sources, the probability of transmitter-internal data corruption is reduced nearly to zero. And by this redundant and independent data verification technique, key-creation process integrity is exported to the receiver.

Communication error correction protocols, however, only validate the data stream from point 20 to point 26 (see FIG. 1). Those skilled in the art will appreciate that not only has conventional transmission error detection been made more robust, but the concept of detection and correction has been extended to the very root of data generation, by the invented method and apparatus. Thus, the requirements for internal data consistency by regulatory bodies such as the FDA and TÜV have been extended to cover the entire data creation-transmission-reception link in vital medical data. Thus, the users of medical patient data, e.g. doctor, nurse, caregiver, are guaranteed the accuracy of the vital patient data just as they would obtain were they in immediate proximity to the patient and patient monitoring system. As a result, the invented method and apparatus meet the most rigorous error correction and safety standards. Those skilled in the art will appreciate that this concept may be extended, without any loss of generality, to cover other items of safety concern such as power monitoring, infusion pump failure, etc.

The invented apparatus will now be described in another way, by reference to FIG. 3. Invented apparatus 48 may be seen from FIG. 3 to include in an illustrative but not limiting ECG monitoring application two independent ECG data buffers 50, 52 within an ECG data monitor/transmitter station 54. It will be appreciated that buffers 50, 52 may be implemented as any one or more memory devices, whether volatile or non-volatile, e.g. magnetic or electronic such as read-and-write memory (RAM), charge-coupled device (CCD), 'flash' memory, etc. Monitor/transmitter station 54 also preferably includes a processor 56, e.g. an appropriately programmed microprocessor executing instructions out of read-only memory (ROM) or a functional equivalent. Processor 56 preferably includes a comparator/validator 58 for contrasting the independent data from buffers 50, 52 to produce a difference signal ("Δ SIGNAL") if any, which is fed to the input of a mixer/packet transmitter. Those of skill in the art will appreciate that the illustrated difference signal, when present, is used by the mixer/packet transmitter to correct transmitter-internal errors prior to the transmission of packetized data over a communication line such as a telephone line.

Buffer 50 is operatively connected with a data packetizer/token generator 60 the packetized/token-appended output of which is fed to a mixer/packet transmitter 62. Buffer 52 is operatively connected with a second data packetizer/token generator 64 the output of which is connected to another input of mixer/packet transmitter 66. The error-corrected output of mixer/packet transmitter 62 is communicated preferably bit-serially over the conventionally schematically illustrated communication line to a remote receiver indicated generally at 66. Preferably, receiver 66 includes a processor 68 such as a ROM-instructed microprocessor and a data display and/or storage and/or hardcopy device 70.

Processor 68 preferably includes a packet receiver 72 and a token validation device 74, the latter of which produces an error signal, if any. It will be appreciated that device 70, within the spirit and scope of the invention, may take any suitable form. For example, it may be a video display terminal (VDT) capable of imaging the monitored data in textual, graphical or any other suitable form. Alternatively, it may be a simple strip chart recorder for graphic ECG waveform hardcopy production or a line printer for textual ECG waveform data hardcopy production. Alternatively, it may be simply a storage device such as any suitable volatile or non-volatile memory device such as tape, disc, CCD, RAM, etc. It will be understood that one prescribed function performed by device 70 is to utilize the error signal produced by token validation device 74 and to correct any discovered errors in the ECG data that is received by packet receiver 72.

Briefly summarizing the invented error detection and avoidance method, dual tokens or checksums are generated from independently stored data buffers and the tokens are compared to ensure their agreement. A single token in agreement with both independently generated tokens then is appended to a single copy of the data packets indicated by the token comparisons to have been in agreement, and the agreeable data packet and its appended agreeable token are transmitted from patient site 12. At a remote overview site, the data packet and its appended token are received and the token is validated before any patient condition is diagnosed or any remedial action is taken. Only if the received token indicates that the received medical patient data are valid would the medical service provider take a remedial action in response to received medical patient data. Of course, it will be appreciated that, most often, medical patient data will be transmitted and received error-free and remedial action taken as indicated. Thus, the invented error detection and avoidance technique gives the highest level of assurance that the right thing is being done for the patient at all times.

The invented apparatus now will be understood to provide concurrent voice and medical data communication over a common link. As illustrated in FIGS. 1 and 3, invented apparatus 48 preferably comprises a life signs monitor 16 at a patient site 12 responsive to a medical patient 14 for producing medical data—e.g. ECG, pulse, bp, blood oxygen or sugar levels, lung capacity, etc.—representative of the patient's life signs; a memory device such as one or more of buffers 50, 52 for storing such medical data; a transmitter 54 for transmitting such medical data from the memory device via a communication line 22; a remote receiver 66 at an overview site 24, receiver 66 being coupled with communication line 22 for receiving such medical data for presentation to a medical service provider 30; and a telephone link such as that illustrated in FIG. 1 and described herein for at least one-way voice communication from service provider 30 to patient 14, with the telephone link utilizing common communication line 22 for such voice communication and such data transmission.

Preferably, the telephone link provides two-way voice communication between service provider 30 and patient 14, although it will be appreciated that perhaps the more important communication is from service provider 30 to patient 14. As described herein, such voice communication from service provider 30 to patient 14 may include instructing patient 14 on the use of monitor 16 or may be of a more general advice or reassurance nature. As described herein, such responsive voice communication from patient 14 to service provider 30 may include status or observation information regarding monitor 16 or may be of a more general nature, e.g. confirmation that patient 14 is taking his or her prescribed medications or information regarding the patient's health. In accordance with the invention, it is possible to provide for two-way, patient site-to-service provider site, voice communication, in addition to patient data transmission from patient site to service provider site over a single, common telephone line that typically is available anywhere within the PSTN.

In accordance with the preferred embodiment of the invention, the memory device includes at least two medical data buffers 50, 52, and transmitter 54 includes a comparator or comparator/validator 58 for generating a difference signal upon detection of a difference between corresponding data within the two buffers. Also in accordance with the preferred embodiment of the invention, transmitter 54 further includes for each of the preferably two medical data buffers 50, 52 a buffered data packetizer and a token generator capable of producing a token symbolizing such packetized buffered medical data, e.g. packetizer/generators 60, 64. Further in accordance with the preferred embodiment of the invention, transmitter 54 further includes a mixer 62 responsive to each of the tokens produced by packetizer/generators 60, 64 and to the difference signal to produce a transmit data packet representing more highly correlated, and thus accurate, medical patient data.

Those of skill will appreciate that, with redundant buffering of what should be identical medical patient data, with comparison thereof and generation of a signal representing any difference therebetween, with using such a difference signal to mix independently generated data packet tokens to produce a single data packet and an appended validation token—as illustrated in FIG. 3 and as described herein—it is possible in accordance with the invention to ensure the very highest possible data integrity for transmission to a remote physician site over a standard voice-grade telephone line.

Further in accordance with the invented apparatus, preferably receiver 66 includes a transmit data packet receiver 72 and a token validator 74 capable of determining whether the transmit data packet received by packet receiver 72 is valid, with token validator 74 producing an error signal for use by receiver 66 to determine whether the data is 'believed' by the independent transmitter and receiver processors to be accurate, in which case the patient data is presented in tabular, graphic or alternative form on a presentation device—e.g. a VDT, printer, strip-chart or magnetic medium recorder, facsimile machine, personal computer (PC), personal digital assistant (PDA) or any other useful recording, output or presentation device—or whether instead the patient data is 'believed' to be suspect in which case the service provider is so informed. Those of skill will appreciate that one or more of such alternative recording, output and presentation devices may be selected at the remote physician site under the automatic switching control of a patient data server device such as a dedicated PC.

Figure 4:
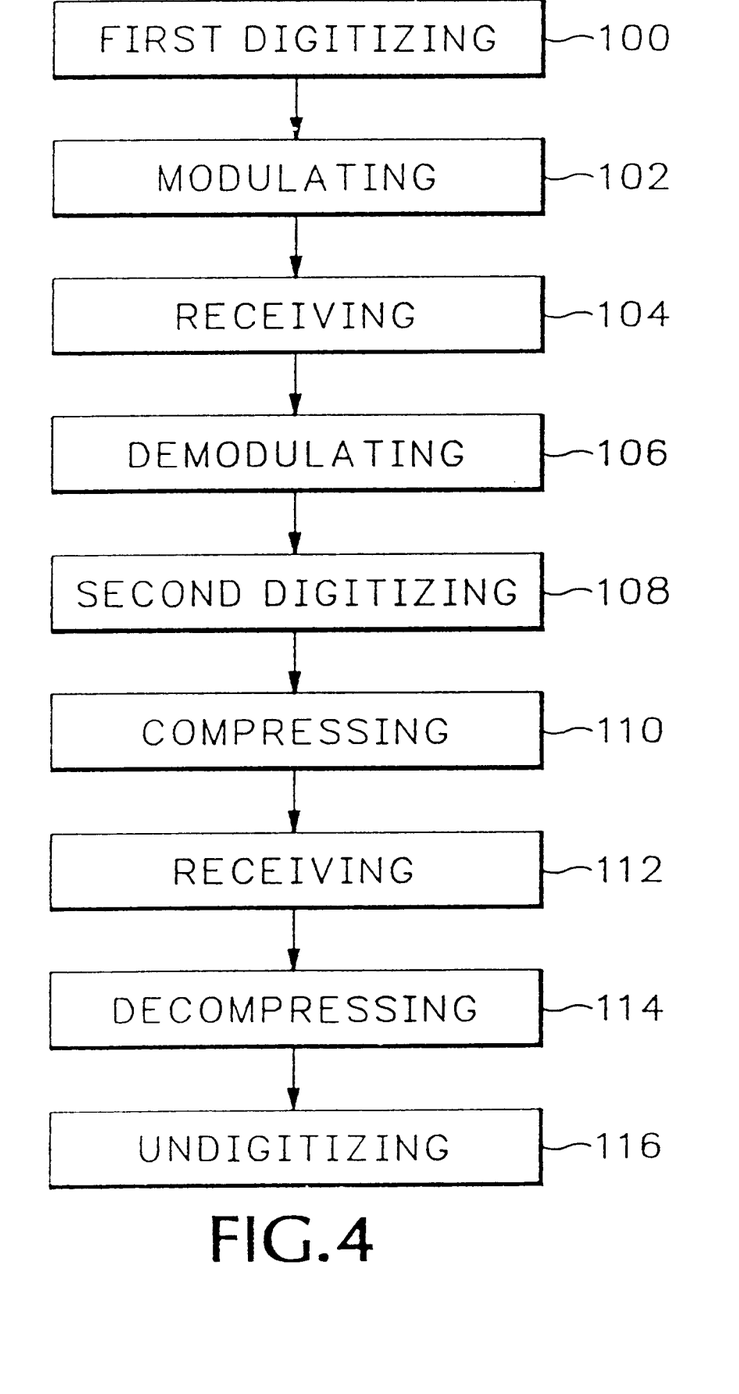
FIG. 4 is a flowchart that illustrates the preferred method of the invention.

Referring next to FIG. 4, the preferred method of the invention now is described. The invented medical patient monitoring method will be understood to be for concurrently communicating physician voice and patient data over a single telephone line. Preferably, the method comprises the following steps: 1) at 100 FIRST DIGITIZING the patient data for transtelephonic communication to a remote monitoring site; 2) at 102 MODULATING a single-line carrier with such digitized data in such manner that the data modulation is substantially inaudible to the physician and to the patient and in such manner as to permit sufficient remnant bandwidth for compressed voice communication; 3) at 104 and 106, respectively, RECEIVING and DEMODULATING such digitized data at such remote monitoring site for physician overview of the patient data; 4) concurrently with FIRST DIGITIZING step 100, MODULATING step 102 and RECEIVING and DEMODULATING steps 104, 106, SECOND DIGITIZING at 108 and COMPRESSING at 110 the physician voice, at such monitoring site, in such manner as to fit within such remnant bandwidth.

The preferred method of the invention further preferably comprises 5) at 112 and 114, respectively, RECEIVING and DECOMPRESSING; and 6) UNDIGITIZING at 116 such digitized and compressed physician voice at patient site 12, thereby permitting concurrent communication of patient data to monitoring site 24 and of physician voice to patient site 12. Those skilled in the art will appreciate that, by performing SECOND DIGITIZING and COMPRESSING steps 108, 110 concurrently with FIRST DIGITIZING, MODULATING, RECEIVING and DEMODULATING steps 100, 102, 104, 106 both patient medical data and physician voice signal may be transmitted (albeit in different directions) within the limited voice bandwidth of a PSTN telephone line, in accordance with invention. Those of skill in the arts also will appreciate that such in accordance with the preferred method of the invention may be performed by apparatus 10 or 48, as illustrated in FIGS. 1 or 3, wherein processors 56 and 68 are suitably programmed to effect such invented method.

Preferably the invented method is adaptive automatically to allocate the single-line bandwidth between patient data and physician voice, wherein a higher patient data communication rate occurs responsive to and concurrent with a lower physician voice communication demand. Such adaptive line bandwidth allocation preferably is accomplished by use of a DSVD device such as DSVD device 28 having a suitably programmed ROM 28a (or, alternatively, suitable hardware or software or any combination thereof), as shown in FIG. 1. By the use of such invented method, those of skill in the art will appreciate that the physician voice, responsive to such overview of the patient data, provides feedback to the patient regarding the patient monitoring, as described above by way of the use model. A typical patient such as patient 14 is equipped with patient life signs monitoring equipment or simply life signs monitor 16 such that the physician voice, responsive to such overview of the patient data, provides instruction to the patient regarding use of such equipment. It will be appreciated by skilled persons that such instruction might include requesting that patient site 12 perform a re-transmission of previously overviewed patient data, as in the case where it is determined by receiver 66 (see FIG. 3), via the illustrated error signal that corrupted medical patient data has been received.

The method preferably further comprises providing for concurrent duplex voice communication concurrent with the patient data communication, wherein patient data, physician voice and patient voice are communicated over the single telephone line such as that illustrated at 22 in FIG. 1 and described herein as typically being a part of the ubiquitous PSTN. Typical of such voice communications, the physician voice, responsive to such overview of the patient data, provides feedback to the patient regarding the patient monitoring. Also typical of such voice communications, the patient voice, responsive thereto, provides acknowledgement to the physician regarding the feedback therefrom. Any and all such one-way or two-way voice communications between patient 14 and service provider 30 are contemplated, and are within the spirit and scope of the invention.

Also in accordance with the invented method, at patient site 12 the patient data is appended with an error correcting code such as either or both tokens produced by packetizer/generators 60, 64 to produce error correction-coded patient data. In such a case, at the monitoring site such error correction-coded patient data is checked, at least, as by use of token validator 74 and the illustrated error signal produced thereby, and corrected as necessary. Thus, the preferred method of the invention further includes patient data error detection including transmission and reception of a validation code that is appended to such digitized data, wherein if a data error is detected then no patient-remedial action is taken.

Those of skill in the art will appreciate that, alternatively or additionally to the illustrated token generation and validation, conventional methods may provide for medical patient data error detection and correction. For example, the error correcting code may take the form of a cyclic redundancy coding (CRC) scheme, as is conventional and as such will not be further described herein. In these and other contexts, the preferred method of the invention may further comprise patient data error correction including re-transmission of previously overviewed patient data via physician voice instruction to the patient site upon detection by the physician of apparently anomalous patient data. Any such medical patient data error avoidance, detection and correction techniques is contemplated and is believed to be within the spirit and scope of the invention.

Thus, those skilled in the art will appreciate that, by common link, single telephone line, single-line carrier, single-line bandwidth and the like is meant conventional PSTN or equivalent conveyance for carrying a single, full-duplex telephone call in which two-way voice communication for years has been provided by local and long-distance telephone companies, whereby separate essentially simplex or half-duplex lines and their attendant cost are obviated. Typically, such PSTN conveyances have been characterized by a single, twisted pair of conductors connected via a dedicated line to a local switching network, wherein two speakers' analog voices signals are picked up by a microphone within a handset; are amplified and transmitted bi-directionally to a remote handset's speaker over a relatively narrow audible frequency range of approximately 1,000–4,000 Hz or a bandwidth of approximately 3,000 Hz. Thus, by single, duplex communication link or line very simply generally is meant the functional equivalent of a single pair of conductors representing a voice and ground wire pair having a characteristic impedance and other electrical parameters that permit coherent, two-way, analog voice communication between two arbitrarily distant telephones. It will be understood that such, within the spirit and scope of the invention, may take an equivalent wireless form such as a single telephone line used in cellular, satellite, fiber-optic or other communications media.

The invention thus may be understood to represent a significant improvement over conventional medical patient monitoring techniques and equipment that provide only for the simplex trans-telephonic communication of patient data. The improvement may be summarized briefly as providing for medical patient data error avoidance, detection and/or correction in a PSTN telephone link-based system that provides not only continuous, real-time patient data, including waveform data, monitoring but also one-way or two-way concurrent voice communication over a common voice-grade line.

Accordingly, while a preferred embodiment of the invention has been described herein, and preferred methods associated therewith, it is appreciated that modifications are possible that are within the scope of the invention.

It is claimed and desired to secure by Letters Patent:

1. A medical patient monitoring and diagnostic method for concurrently communicating physician voice, patient voice and real-time patient data over a single communication link, the method comprising:

obtaining real-time patient data from patient life signs equipment operatively connected to a patient, wherein the patient data includes waveform data;

first digitizing the patient data and the patient voice for communication to a remote monitoring site by transmission over said single single communication link;

modulating a single carrier with such digitized data in such manner that the data modulation is substantially inaudible to the physician and to the patient and in such manner as to permit sufficient remnant bandwidth for compressed physician and patient voice communication;

receiving and demodulating such digitized real-time patient data and patient voice at such remote monitoring site for physician overview of the patient data, wherein the patient data is received at the remote monitoring site within real-time limits of when it was obtained from the patient life signs equipment;

concurrently with said first digitizing, said modulating and said receiving and demodulating, providing for voice communication concurrent with the real-time patient data communication by second digitizing and compressing the physician voice, at such monitoring site, in such manner as to fit within such remnant bandwidth; and receiving and decompressing and undigitizing such digitized and compressed physician voice at the patient site, thereby permitting concurrent communication of patient data and patient voice and physician voice over a single communication link.

2. The method of claim 1, wherein the step of obtaining real-time patient data includes obtaining ECG waveform data.

3. The method of claim 1, wherein the step of obtaining real-time patient data includes obtaining 12-lead ECG waveform data.

4. The method of claim 1, wherein the physician receives the patient data within seconds of when it was obtained by the patient life signs equipment.

5. The method of claim 1, wherein the patient data and patient voice are synchronized with each other.

6. The method of claim 1, wherein said method is adaptive automatically to allocate the single-line bandwidth between patient data and physician voice, wherein a higher patient data communication rate occurs responsive to and concurrent with a lower physician voice communication demand.

7. The method of claim 1, wherein the physician voice, responsive to such overview of the patient data, provides feedback to the patient regarding the patient monitoring.

8. The method of claim 7 in which the patient is equipped with patient life signs equipment, wherein the physician voice, responsive to such overview of the patient data, provides instruction to the patient regarding use of such equipment.

9. The method of claim 8, wherein such instruction includes requesting that the patient site perform a re-transmission of previously overviewed patient data.

10. The method of claim 1, wherein the physician voice, responsive to such overview of the patient data, provides feedback to the patient regarding the patient monitoring and wherein the patient voice, responsive thereto, provides acknowledgement to the physician regarding the feedback therefrom.

11. The method of claim 1 which further comprises detecting patient data errors including transmission and reception of a validation code that is appended to such digitized data, wherein if a data error is detected then no patient-remedial action is taken.

12. The method of claim 1 which further comprises detecting patient data errors including re-transmission of previously overviewed patient data via physician voice instruction to the patient site upon detection by the physician of apparently anomalous patient data.

13. Apparatus for providing real-time voice and real-time medical data communication concurrently over a common link, the apparatus comprising;

life signs equipment at a patient site responsive to a medical patient for producing real-time medical data, including waveform data;

a telephone link for at least one-way voice communication between the service provider and the patient, said telephone link utilizing a communication line for such voice communication;

a converter for digitizing said voice communication;

a transmitter for transmitting such real-time medical data and digitized voice communication concurrently via the communication line; and a remote receiver at an overview site, said receiver being coupled with the communication line for receiving such medical data for presentation to a medical service provider, wherein the patient data is received at the overview site within real-time limits of when it was obtained from the life signs equipment.

14. The apparatus of claim 13, wherein said telephone link provides two-way voice communication between the service provider and the patient.

15. The apparatus of claim 13, wherein the apparatus further includes a memory device for storing said medical data, wherein said memory device includes at least two medical data buffers and wherein said titter includes a comparator for generating a difference signal upon detection of a difference between corresponding data within said two buffers.

16. The apparatus of claim 15, wherein said transmitter further includes for each of said medical data buffers a buffered data packetizer and a token generator capable of producing a token symbolizing such packetized buffered medical data, and wherein said transmitter further includes a mixer responsive to each of said tokens and to said difference signal to produce a transmit data packet representing more highly correlated medical patient data.

17. The apparatus of claim 16, wherein said receiver includes a transmit data packet receiver and a token validator capable of determining whether said transmit data packet is valid, said token validator producing an error signal for use by said receiver to determine whether the transmitted data packet is valid.

18. The apparatus of claim 13, wherein the patient data includes 12-lead ECG waveform data.

19. The apparatus of claim 13, wherein the apparatus is adapted to transmit the patient data to the remote receiver within seconds of when it was obtained by the life signs equipment.

20. The apparatus of claim 13, wherein the apparatus is adapted to a synchronize the patient data and patient voice with each other.

21. The apparatus of claim 13, wherein the converter is adapted to digitize both the medical data and the voice communication.

22. The apparatus of claim 13, wherein the transmitter is adapted to automatically allocate(s) the bandwidth of the communication line between the medical data and the voice communication responsive to the bandwidth demands of the medical data and the voice communication.

23. Apparatus for providing real-time voice and medical data communication over a common link the apparatus comprising:

life signs equipment at a patient site responsive to a medical patient for producing medical data, including waveform data;

a memory device for storing such medical data, wherein said memory device includes at least two medical data buffers, a transmitter for transmitting such medical data from the memory device via a communication line, wherein said transmitter includes a comparator for generating a difference signal upon detection of a difference between corresponding data within said two buffers;

a remote receiver at an overview site, said receiver being coupled with the communication line for receiving such medical data for presentation to a medical service provider; and a telephone link for at least one-way voice communication between the service provider and the patient, said telephone link utilizing said communication line for such voice communication, wherein the patient data is received at the overview site within real-time limits of when it was obtained from the life signs equipment.

24. The apparatus of claim 23, wherein said transmitter further includes for each of said medical data buffers a buffered data packetizer and a token generator capable of producing a token symbolizing such packetized buffered medical data, and wherein said transmitter further includes a mixer responsive to each of said tokens and to said difference signal to produce a transmit data packet representing more highly correlated medical patient data.

25. The apparatus of claim 24, wherein said receiver includes a transmit data packet receiver and a token validator capable of determining whether said transmit data packet is valid, said token validator producing an error signal for use by said receiver to determine whether the transmitted data packet is valid.

* * * * *

UNITED STATES PATENT AND TRADEMARK OFFICE
CERTIFICATE OF CORRECTION

PATENT NO. : 5,941,829
DATED : August 24, 1999
INVENTOR(S) : Saltzstein et al.

It is certified that error appears in the above-identified patent and that said Letters Patent is hereby corrected as shown below:

Column 16,
Line 60, "titter" should be -- transmitter --.

Column 17,
Line 18, "to a synchronize" should be -- to synchronize --.

Column 18,
Line 3, the comma "," should be a semi-colon -- ; --.

Signed and Sealed this

First Day of January, 2002

Attest:

JAMES E. ROGAN
Attesting Officer   Director of the United States Patent and Trademark Office